US009561008B2

(12) United States Patent
Neethimanickam et al.

(10) Patent No.: US 9,561,008 B2
(45) Date of Patent: Feb. 7, 2017

(54) METHOD OF DISPLAYING IMAGE

(75) Inventors: Antony Kalugumalai Neethimanickam, Bangalore (IN); Ganesh Kumar Mohanur Raghunathan, Bangalore (IN)

(73) Assignee: General Electric Company, Schenectady, NY (US)

( * ) Notice: Subject to any disclaimer, the term of this patent is extended or adjusted under 35 U.S.C. 154(b) by 201 days.

(21) Appl. No.: 13/328,022

(22) Filed: Dec. 16, 2011

(65) Prior Publication Data

US 2012/0163536 A1 Jun. 28, 2012

(30) Foreign Application Priority Data

Dec. 28, 2010 (IN) .......................... 3992/CHE/2010

(51) Int. Cl.
*A61B 6/00* (2006.01)
(52) U.S. Cl.
CPC ................. *A61B 6/42* (2013.01); *A61B 6/461* (2013.01); *A61B 6/5211* (2013.01)
(58) Field of Classification Search
CPC ........... A61B 6/465; A61B 6/42; A61B 6/461; A61B 6/5211
USPC .................................................. 378/62, 98.8
See application file for complete search history.

(56) References Cited

U.S. PATENT DOCUMENTS

| 4,627,020 | A | 12/1986 | Anderson et al. |
| 4,689,824 | A | 8/1987 | Mitchell et al. |
| 5,111,192 | A | 5/1992 | Kadakia |
| 5,295,237 | A | 3/1994 | Park |
| 5,479,525 | A | 12/1995 | Nakamura et al. |
| 2003/0016786 | A1 | 1/2003 | Horbaschek |
| 2003/0169847 | A1* | 9/2003 | Karellas et al. ............. 378/98.3 |
| 2006/0113481 | A1* | 6/2006 | Murphy et al. .......... 250/370.09 |
| 2007/0081627 | A1* | 4/2007 | Bates ..................... G01N 23/04 378/62 |
| 2008/0232717 | A1 | 9/2008 | Nishimura et al. |
| 2009/0016580 | A1 | 1/2009 | Yamamichi et al. |
| 2009/0096814 | A1* | 4/2009 | Nagaraj et al. ............... 345/659 |
| 2010/0329532 | A1* | 12/2010 | Masuda et al. ............... 382/132 |
| 2011/0075812 | A1* | 3/2011 | Takekoshi et al. .......... 378/98.8 |

FOREIGN PATENT DOCUMENTS

| CN | 101141917 A | 3/2008 |
| JP | 2010133982 A | 6/2010 |

OTHER PUBLICATIONS

Unofficial English translation of Office Action and Search Report issued in connection with corresponding CN Application No. 201110462054.6 on Oct. 10, 2014.
Siemens, "Artis Zeego Multiaxis System", http://www.medical.siemens.com/webapp/wcs/stores/servlet/ProductDisplay~q_catalogId~e_-11~a_catTree~e_100010,1007660,12751,14412~a_langId~e_-11~a_productId~e_181902~a_storeId~e_10001.htm.

\* cited by examiner

*Primary Examiner* — David J Makiya
*Assistant Examiner* — Dani Fox
(74) *Attorney, Agent, or Firm* — GE Global Patent Operation; Marc A. Vivenzio

(57) ABSTRACT

In one embodiment, a method of displaying image in an imaging system is provided. The method comprises steps obtaining an image from an radiation detector, receiving a selection for orientation from a user, mechanically rotating the radiation detector based on the selection for orientation and performing a digital image rotation on the image complementing the mechanical rotation of the radiation detector such that the image is rotated to the orientation selected by the user and displaying the image.

16 Claims, 6 Drawing Sheets

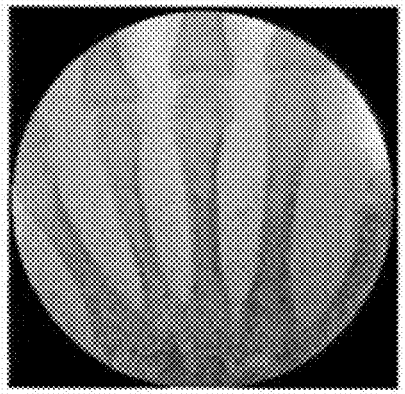
FIG. 3(a)　　　　FIG. 3(b)
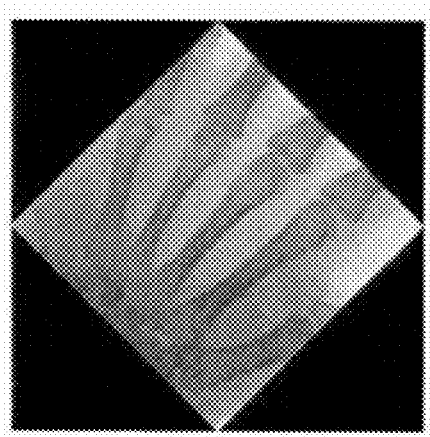
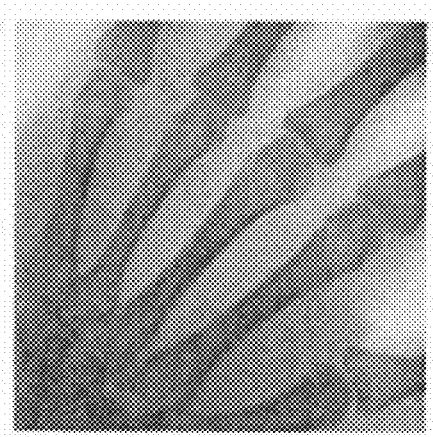
FIG. 4(a)　　　　FIG. 4(b)

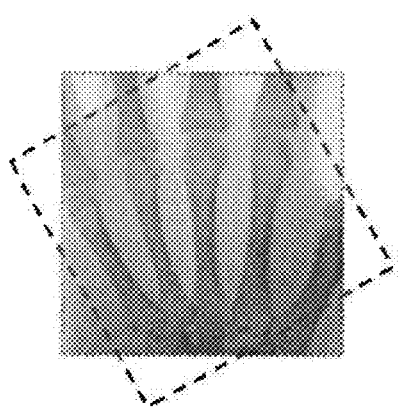 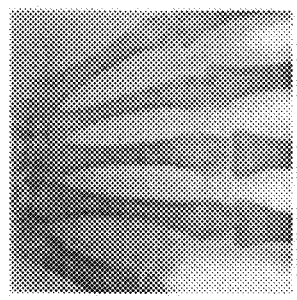 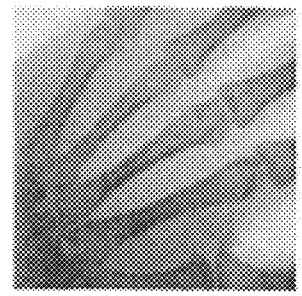
FIG. 5(a)  　　　FIG. 5(b)  　　　FIG. 5(c)
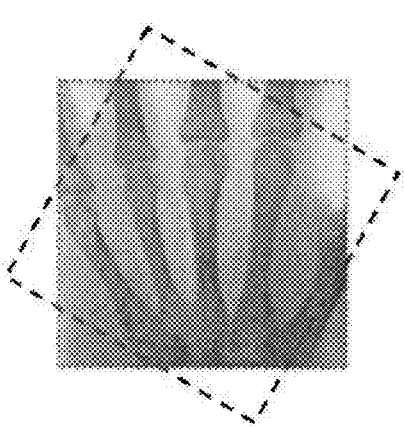 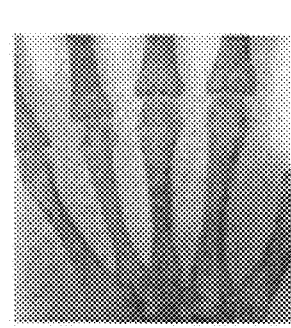 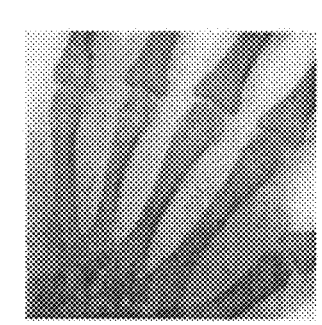
FIG. 6(a)  　　　FIG. 6(b)  　　　FIG. 6(c)

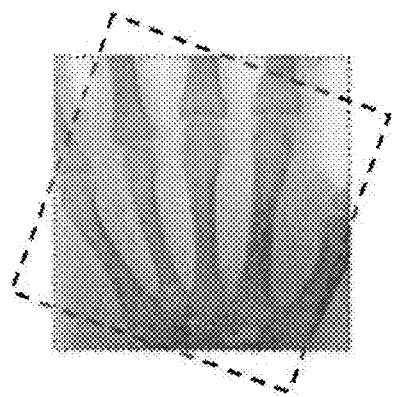 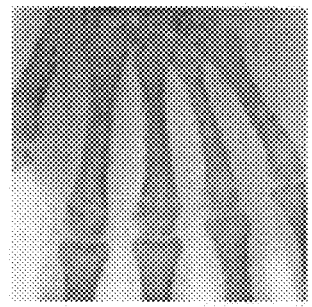 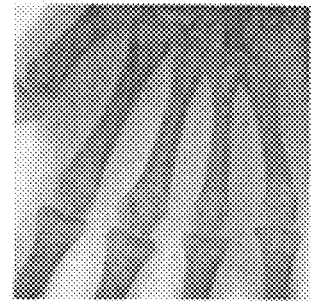
FIG. 7(a)  FIG. 7(b)  FIG. 7(c)
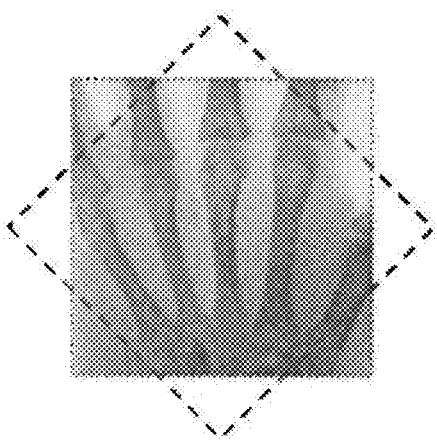 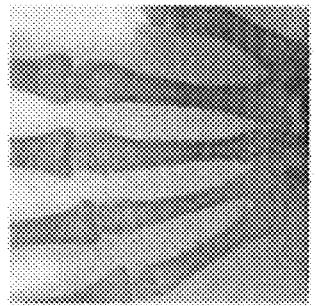 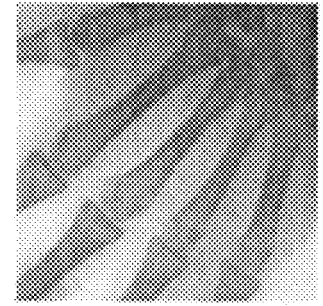
FIG. 8(a)  FIG. 8(b)  FIG. 8(c)

METHOD OF DISPLAYING IMAGE

FIELD OF INVENTION

The invention generally relates to radiation-based imaging, 2D planar x-ray imaging and more particularly to digital image processing methods in radiation-based imaging.

BACKGROUND OF THE INVENTION

Conventionally images from Image Intensifier (II) are circular as the geometry of Image Intensifier (II) is circular. Hence the image formed by imager is circular and rotation is achieved either by mechanically rotating a charge coupled device that is coupled to the image intensifier or by digitally rotating the images in software.

On the other hand, a square Flat Panel Detector (FPD) when rotated digitally poses problems in displaying the rotated image. Since the diagonal of a square is of length √2*L (L is the side of the square), in order to display the image from square flat panel detector a display size capable of accommodating diagonal of the square is to be provided. Alternatively, in order to display the entire image one needs to shrink or crop the rotated image.

However, regulations in medical industry constrain cropping images that are obtained by exposure to radiation. This disadvantage leaves the user with two options, either shrinking the rotated image prior to displaying or restricting the exposure to a centered circle (by applying a circular mask). The limitation in using these methods is shrinking the displayed image results in variation of the image size along with the angle of rotation thereby causing degradation of obtained image quality. Further, applying a circular mask impacts effective area usage. The effective area usage of the flat panel detector reduces significantly (by 21.5 percent) with a circular mask.

Some of the prior art methods suggest achieving image rotation either by rotating flat panel detector mechanically by 360° or by performing digital image rotation. One of the challenges in such methods is performing a 360° mechanical rotation of the flat panel detector. Further, digital rotation too has its impact on Image Quality (Interpolation loss/artifacts, cropping of image corners or shrinking the image size) as explained above.

Using such methods for image processing and display, the user is forced to choose between image size and field of view.

Hence there exists a need for an efficient and improved method of processing and displaying an image that overcomes the drawbacks of digital rotation with square images, and which also maintains the image size while providing increased field of view.

BRIEF DESCRIPTION OF THE INVENTION

The above-mentioned shortcomings, disadvantages and problems are addressed herein which will be understood by reading and understanding the following specification.

In one embodiment, a method of displaying image in an imaging system is provided. The method comprises steps obtaining an image from a radiation detector, receiving a selection for orientation from a user, mechanically rotating the radiation detector based on the selection for orientation and performing a digital image rotation on the image complementing the mechanical rotation of the radiation detector such that the image is rotated to the orientation selected by the user and displaying the image.

Systems and methods of varying scope are described herein. In addition to the aspects and advantages described in this summary, further aspects and advantages will become apparent by reference to the drawings and with reference to the detailed description that follows.

BRIEF DESCRIPTION OF THE DRAWINGS

FIGS. 3-4 show comparison between image obtained in prior art and image obtained by using the method of FIG. 1; and FIGS. 5-8 show a sequence of images obtained by using the method described in FIG. 1 for various orientation selections.

DETAILED DESCRIPTION OF THE INVENTION

Figure 1:
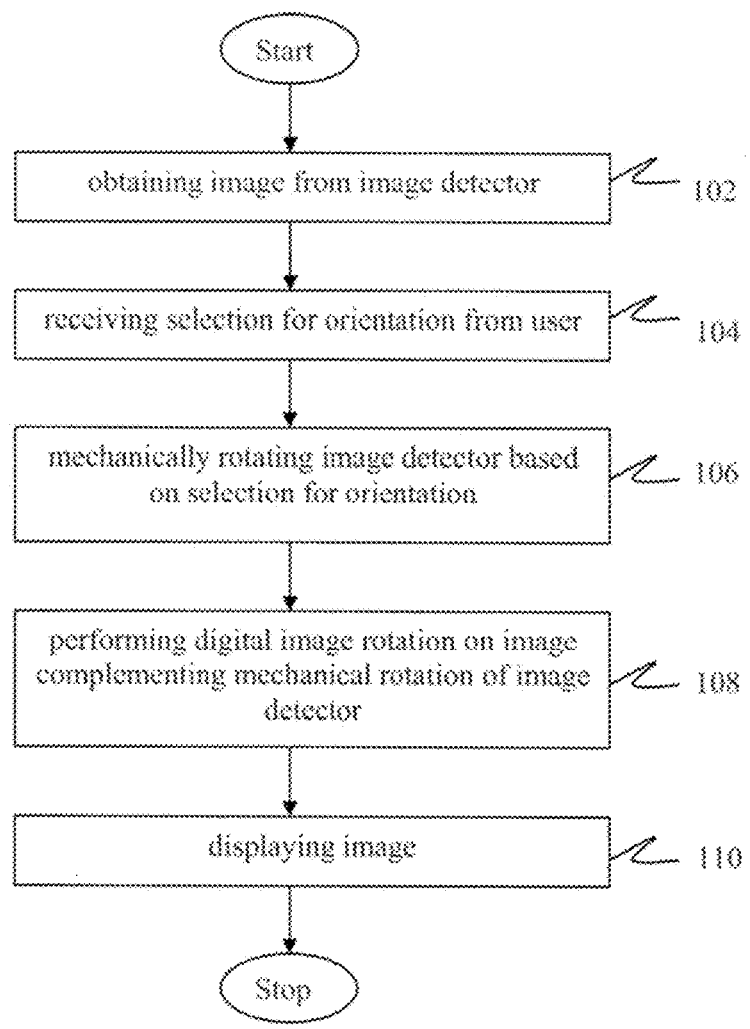
FIG. 1 shows a flow diagram depicting a method of displaying image as described in an embodiment.

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

An imaging system configured for performing x-ray fluoroscopic imaging uses a radiation source and a radiation detector. A C-arm configuration of the imaging system allows the oblique positioning of the projection system by aligning the radiation source and the radiation detector assembly. It further rotates the radiation source and the radiation detector about an object positioned on a support surface to provide multi-directional viewing of the object. The object can be an animated or an in-animated object.

When the object is irradiated with the x-ray energy, a percentage of the x-rays reaching the object are absorbed by the object's body, the amount of absorption depending on the tissue upon which the x-rays are incident. Since x-rays generally travel in a straight line, the x-ray energy exiting the object's body on the side of the body away from the source is a spatial representation of absorption in the objects body, and therefore of relative tissue and skeletal densities.

To receive the x-rays passing through the object's body, the radiation detector comprises a scintillation screen, provided on the side of the object away from the x-ray source. The scintillation screen, is a fluorescent material sensitive to x-rays, and when it receives x-ray energy it re-radiates visible light. The spatial intensity patterns of the radiation emitted from the scintillation screen is proportional to the spatial intensity pattern of the x-ray radiation received by the screen. Thus the scintillation screen provides an image in the visible spectrum, or alternating in the ultraviolet or near infrared, which is regionally proportional to the x-ray image reaching the scintillation screen.

The radiation detector further comprises an images sensor, such as, for example, a charge coupled device (CCD) or CMOS sensors. The image sensor receives radiation from the scintillation screen. The CCD image sensor is an array of photosensitive pixels, which convert photons to electrons and thereby generate a discrete electronic representation of a received optical image. A fiber optic screen focuses the visible light emitted from the scintillation screen, onto the surface of the CCD image sensor.

After termination of the x-ray exposure, the discrete representation in the CCD is read out by an electronic controller. The electronic controller reads the image representation from the CCD image sensor pixel by pixel and organizes it into a digital array. The digital array, representing spatial position and x-ray intensity, is then output to an image memory or an image buffer. From the image buffer, the image can be accessed by a data processing unit for performing image processing techniques. A cathode ray tube (CRT), a LED (light emitting diode), a LCD (liquid crystal display) or other type of electronic image display is also provided to allow the image to be displayed before or following processing by the data processing unit.

In one embodiment, the radiation detector comprises a flat panel detector. Flat panel detectors have a number of advantages over image intensifiers. Some of the advantages include low dose irradiation compared to its inherently high detective quantum efficiency (DQE), compact in size and hence reduced weight, increased field of view (FOV) as against a circular image intensifier and immunity to external magnetic field which causes a distortion in the images.

In one embodiment, the invention describes a method of displaying image using image rotation without affecting the quality of the image. The image rotation is achieved by a combination of mechanical rotation of the flat panel detector (referred to hereafter as FPD) and digital image rotation in multiples of 90 degrees. Further, the mechanical rotation of the flat panel detector is simplified in which the maximum rotation that is carried out is within the range of 45 degrees in clockwise and counter clockwise direction, about the rotational axis. The flat detector is mounted such that it can rotate about the rotational axis.

This method overcomes the problems with loss of image quality associated with digital image rotation for images obtained from a square flat panel detector (interpolation artifacts due to rotation and resizing) and simplifies the mechanical complexity greatly by restricting the rotation of the flat panel detector to 45 degrees. Any degree (0-360) of image rotation can be achieved by rotating the flat panel detector and a suitable combination of digital image rotation in multiples of 90 degrees.

Figure 9:
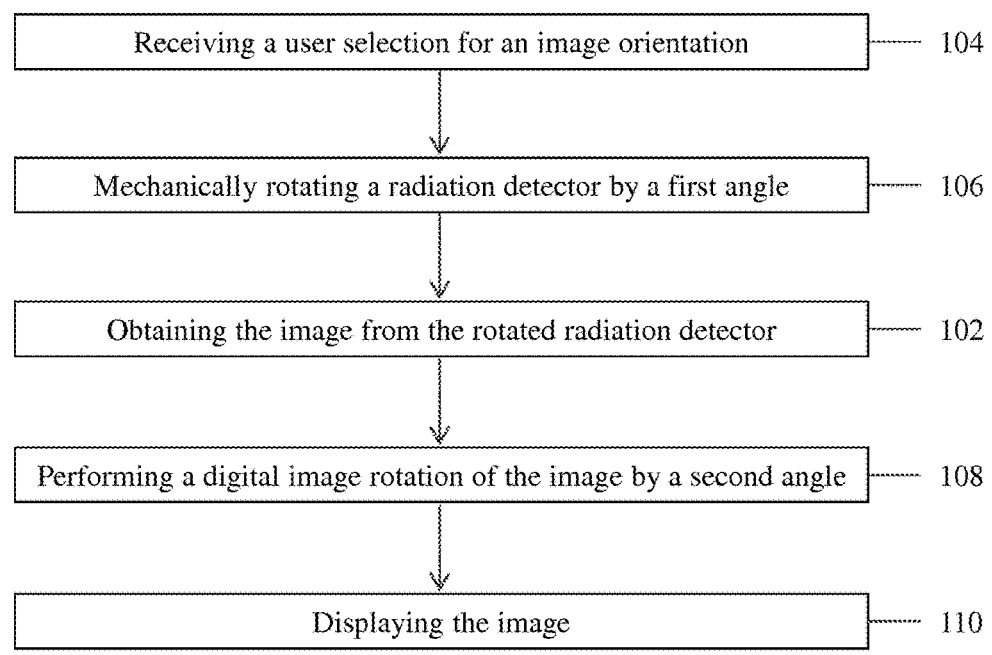
FIG. 9 is a flow diagram depicting a method of displaying an image as described in an embodiment.

In one embodiment, as shown in FIG. 1, a method 100 of displaying image in an imaging system is provided. The method 100 comprises steps of obtaining an image from an radiation detector at step 102, receiving a selection for orientation from a user at step 104, mechanically rotating the radiation detector based on the selection for orientation at step 106, performing a digital image rotation on the image complementing the mechanical rotation of the radiation detector such that the image is rotated to the orientation selected by the user at step 108 and displaying the image at step 110. See also FIG. 9.

In one embodiment, where the detector is a flat panel detector having a square shape, the method 100 comprises mechanically rotating the radiation detector in the range of about 0 degree to about 45 degrees in at least one of the clockwise and counterclockwise directions.

In another embodiment, where the detector is a flat panel detector having a rectangular shape, the method 100 comprises mechanically rotating the radiation detector in the range of about 0 degree to about 90 degrees in at least one of the clockwise and counterclockwise directions.

Figure 2:
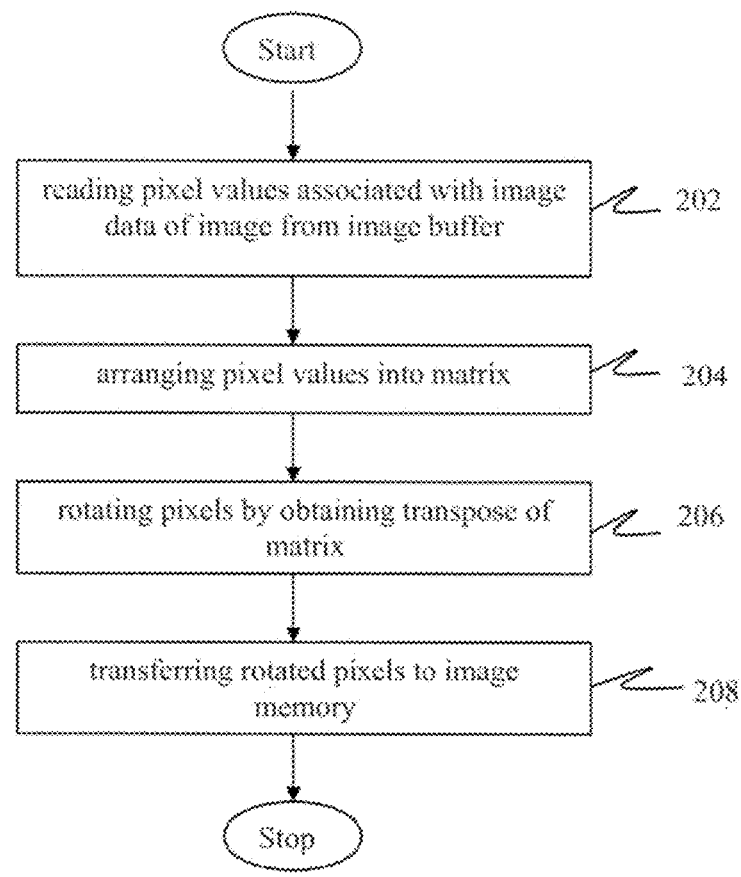
FIG. 2 shows a flow diagram depicting a method of performing digital image rotation as described in an embodiment.

In one embodiment, as shown in FIG. 2, the method 200 of performing the digital image rotation comprises steps of rotating the image in multiples of 90 degrees. The method 200 comprises steps of reading one or more pixel values associated with an image data of the image from an image buffer at step 202, arranging the pixel values into a matrix at step 204, rotating the pixels by obtaining transpose of the matrix based one of a 90 degree rotation, a 180 degree rotation, and a 270 degree rotation at step 206 and transferring the rotated pixels to an image memory at step 208.

Further, the method of obtaining the image at step 102 comprises steps of providing a radiation source such that radiation emitted by the source is transmitted through an object onto a scintillator, providing a plurality of image sensors, each image sensor having a two dimensional array of pixel elements that detect light from the scintillator that is emitted in response to radiation from the radiation source, positioning the object on a support table, directing the radiation through the ROI of the object onto the scintillator which emits a spatial intensity pattern of light that is detected by the image sensors, the spatial intensity pattern being coupled to the image sensors with an optical system, binning charge from separate pixel elements of the image sensors for readout with an electronic controller and forming an image of the ROI from the binned representation.

FIG. 3 (a) illustrates the image obtained by applying circular mask to the image obtained from the flat panel detector and FIG. 3 (b) illustrates the image obtained by using the method 100.

FIG. 4(a) shows an image digitally rotated by 45 degree without cropping. This clearly illustrates the reduction in image size in order to accommodate the rotated image as well as 50% reduction in the effective display area.

FIG. 4(b) shows the image that is obtained following the 45-degree rotation using the method 200. This demonstrates increase in field of view, effective utilization of display area and fixed image size.

In each of the FIGS. 5(a), 6(a), 7(a) and 8(a) the physical rotation of the flat panel detector is depicted with dotted outline, FIGS. 5(b), 6(b), 7(b) and 8(b) show the digital rotation in multiples of 90 degrees and the images shown in FIGS. 5(c), 6(c), 7(c) and 8(c) are the displayed or obtained images.

Depending on the mechanical rotation of the flat panel detector in each case selected by the user, the system records this angle and selects a matching angle for digital image rotation. This is illustrated with a series of examples explained in conjunction with FIGS. 5-8.

In one exemplary embodiment, the received selection for orientation is 60 degrees in clockwise direction. This is achieved by rotating the flat panel detector in counter clockwise direction by 30 degrees, subsequently digitally rotating the image from flat panel detector in clockwise direction by 90 degrees. The resultant image has the orientation of 60 degrees (−30°±90°=60°), for example, see FIG. 9.

In another exemplary embodiment, the received selection for orientation is 30 degrees in clockwise direction. This is achieved by rotating the flat panel detector in clockwise direction by 30 degrees, subsequently, digitally rotating the image from flat panel detector in clockwise direction by 0 degrees. The resultant image has the orientation of 30 degrees (30°±0°=30°).

In yet another exemplary embodiment, the received selection for orientation is 200 degrees in clockwise direction.

This is achieved by rotating the flat panel detector in clockwise direction by 20 degrees, subsequently, digitally rotating the image from flat panel detector in clockwise direction by 180 degrees. The resultant image has the orientation of 200 degrees (20°±180°=200°).

In yet another exemplary embodiment, the received selection for orientation is 135 degrees in counter clockwise direction. This is achieved by rotating the flat panel detector in counter clockwise direction by 45 degrees, subsequently, digitally rotating the image from flat panel detector in counter clockwise direction by 90 degrees. The resultant image has the orientation of 135 degrees (−45°−90°=−135°)

In one embodiment, a hardware and software approach is used to image a portion of an object that is larger than the field of view. The larger field of view is obtained by the mechanical rotation of the flat panel detector. The source and detector are advantageously maintained in a given position while performing mechanical rotation of the flat panel detector over the requisite angular range. The translational movement of the flat panel detector can be controlled by a computerized motor control system.

The method described herein uses a combination of mechanical rotation of the flat panel detectors and digital rotation of the image, which help in preserving the image quality.

The other advantages of the method include complete utilization of display or monitor area, increased field of view (FOV), static displayed image outline, eliminates the need for complex algorithms or computations when compared to other digital rotation methods, improves image quality, enables real time imaging, no loss of image data due to interpolation following rotation, does not involve resizing of image and hence no variation in zoom factor, full rotation can be achieved by physical rotation of flat panel detector within 0 to 45 degrees in square shaped FPD and 0 to 90 degrees in rectangle shaped FPD in one of the clockwise or counter clockwise directions and simplified mechanical complexity of the flat panel detector rotation.

It will be understood by those skilled in the art that although the particular embodiments shown and described herein relate in general to x-ray imaging applications, it will further be understood that the principles of the present invention may also be extended to other medical and non-medical imaging applications including medical imaging systems, cine imaging, fluoroscopy imaging, pipeline imaging using multiple radiation sources and radiation detectors in a single imaging system, industrial inspection systems and security scanners.

This written description uses examples to describe the object matter herein, including the best mode, and also to enable any person skilled in the art to make and use the object matter. The patentable scope of the object matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method of acquiring an image of a portion of an object that is larger than a field of view, the image for display in an imaging system, the method comprising:
   receiving a selection for orientation from a user;
   mechanically rotating a radiation detector about an axis perpendicular to a detection surface of the radiation detector, based on the orientation selected by the user to an intermediate orientation that provides a larger field of view for the portion of the object, wherein the intermediate orientation is different from the orientation selected by the user;
   obtaining an image from the mechanically rotated radiation detector at the intermediate orientation; and
   performing a digital image rotation on the obtained image complementing the mechanical rotation of the radiation detector such that the obtained image is rotated to the orientation selected by the user.

2. The method of claim 1, further comprising mechanically rotating the radiation detector in the range of about 0 degree to about 45 degrees in at least one of the clockwise and counterclockwise directions.

3. The method of claim 2, wherein the detector is a flat panel detector having a square shape.

4. The method of claim 1, further comprising mechanically rotating the radiation detector in the range of about 0 degree to about 90 degrees in at least one of the clockwise and counterclockwise directions.

5. The method of claim 4, wherein the detector is a flat panel detector having a rectangular shape.

6. The method of claim 1, wherein performing the digital image rotation comprises rotating the image in multiples of 90 degrees.

7. The method of claim 6, further comprising the steps of:
   reading one or more pixel values associated with an image data of the image from an image buffer;
   arranging the pixel values into a matrix;
   rotating the pixels by obtaining transpose of the matrix based one of a 90 degree rotation, a 180 degree rotation, and a 270 degree rotation; and
   transferring the rotated pixels to an image memory.

8. The method of claim 1, wherein obtaining the image comprises steps of:
   providing a radiation source such that radiation emitted by the source is transmitted through an object onto a scintillator;
   providing a plurality of image sensors, each image sensor having a two dimensional array of pixel elements that detect light from the scintillator that is emitted in response to radiation from the radiation source;
   positioning the object on a support surface;
   directing the radiation through the ROI of the object onto the scintillator which emits a spatial intensity pattern of light that is detected by the image sensors, the spatial intensity pattern being coupled to the image sensors with an optical system;
   binning charge from separate pixel elements of the image sensors for readout with an electronic controller; and
   forming an image of the ROI from the binned representation.

9. The method of claim 1, wherein the image sensor comprises one of a two dimensional array of MOS capacitors and a charge coupled device (CCD) that includes a plurality of interpixel channels.

10. The method of claim 1, wherein the optical sensing system is a fiber optic coupler between the scintillator and the image sensor.

11. The method of claim 2, wherein performing the digital image rotation comprises rotating the image in multiples of 90 degrees.

12. A method of providing an image of a portion of an object that is larger than a field of view, the image for display in an imaging system, the method comprising:
   receiving a user selection for an image orientation, wherein the selected orientation requires an image to be rotated by a corresponding total angle in order for the image to be set in the selected orientation;

mechanically rotating a radiation detector about an axis perpendicular to a detection surface of the radiation detector, based on the selected orientation by a first angle, wherein the first angle provides a larger field of view for the portion of the object, wherein the first angle is different from the total angle;

obtaining the image from the mechanically rotated radiation detector at the first angle; and performing a digital image rotation of the obtained image by a second angle, complementing the mechanical rotation of the radiation detector, wherein the sum of the first angle and the second angle is the total angle.

13. The method of claim 12, further comprising:
displaying the entire obtained image.

14. The method of claim 1, further comprising:
displaying the entire obtained image.

15. The method of claim 1, further comprising:
displaying the entire obtained image with the image size of the obtained image.

16. The method of claim 12, further comprising:
displaying the entire obtained image with the image size of the obtained image.

* * * * *